(12) United States Patent
Nagatsuka et al.

(10) Patent No.: US 6,914,077 B2
(45) Date of Patent: Jul. 5, 2005

(54) MITE REPELLANT AND/OR MITICIDE COMPOSITION

(75) Inventors: Michiko Nagatsuka, Tokyo (JP); Hirohiko Ishida, Tokyo (JP); Hiromi Kubota, Tochigi (JP); Ryoichi Hirayama, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/102,711

(22) Filed: Mar. 22, 2002

(65) Prior Publication Data

US 2002/0193437 A1 Dec. 19, 2002

(30) Foreign Application Priority Data

Mar. 29, 2001 (JP) ........................................ 2001-094696
Dec. 7, 2001 (JP) ........................................ 2001-373554

(51) Int. Cl.⁷ ........................ A01N 37/00; A01N 31/00; A61K 31/19; A61K 31/20; A61K 31/045
(52) U.S. Cl. ........................................ 514/557; 558/739
(58) Field of Search ................................ 514/557, 558, 514/739

(56) References Cited

U.S. PATENT DOCUMENTS 5,300,489 A * 4/1994 Boden et al. .................. 512/8
6,080,792 A 6/2000 Zochi et al.

FOREIGN PATENT DOCUMENTS

| JP | 63104905 | | 5/1988 |
| JP | 02264703 | * | 10/1990 |
| JP | 05208902 | * | 8/1993 |
| WO | WO 87/04591 | | 8/1987 |
| WO | WO8704591 | | 10/1988 |
| WO | WO 94/24862 | | 11/1994 |
| WO | WO9424862 | | 11/1994 |
| WO | 9424862 | * | 11/1994 |
| WO | WO0100049 | | 1/2001 |
| WO | WO 01/00049 | | 1/2001 |
| WO | WO0113726 | | 3/2001 |
| WO | WO 01/13726 | | 3/2001 |

OTHER PUBLICATIONS

Phytochemistry (1998), 1999, 50(3), 401–405.
Chemical Abstract n130:193086.
Chemical Abstract 120:71533.
W. Lwande, et al., Database CA Online Chemical Abstract, AN. 1999–95548, XP–002197297, pps. 1–2, "Gynandropsis Gynandra Essential Oil and its Constituents as Tick (Rhipicephalus Appendiculatus) Repellents", 1998.
Chemical Abstracts, AN. 2001–479715, XP–002197298, JP 2001–181110, Jul. 3, 2001.
M. Yatagai, et al., Database CA Online Chemical Abstract, AN. 1994–71533, XP–002197299, pps. 1–2, "Biological Activities And Utilization of Terpenes", 1991.
Derwent Abstract, AN. 1988–165717, XP–002197300, JP 63–104905, May 10, 1988.

* cited by examiner

*Primary Examiner*—Alton Pryor
(74) *Attorney, Agent, or Firm*—Oblon, Spivak, McClelland, Maier & Neustadt, P.C.

(57) ABSTRACT

A mite repellant and/or miticide composition comprising at least one compound selected from the group consisting of jasmonoide, linear sesquiterpene alcohol and linear diterpene alcohol.

The mite repellant and/or miticide composition according to the invention has excellent repellent effect, growth-inhibiting effect and mite repellant and/or miticide effect on mites inhabiting houses.

25 Claims, No Drawings

MITE REPELLANT AND/OR MITICIDE COMPOSITION

BACKGROUND OF THE INVENTION

1. Field of the Invention

The present invention relates to a mite repellant and/or miticide composition having an excellent anti-mite effect on mites infesting houses.

2. Discussion of the Background

A great number of the mites inhabit places poor in air permeability, such as interiors of carpets, sofas, blankets, comforters and bedclothes or mattresses. The mites in houses can form the cause of allergic disease such as bronchial asthema and allergic rhinitis, and dermatisis, and so various exterminators have been developed.

As mite repellant and/or miticide compositions, are used various kinds of agents such as pyrethroids, carbamates and organophosphorus compounds. However, these agents are high in toxicity and are not preferable from the viewpoint of safety in houses, particularly, homes having children. These conventional mite repellant and/or miticide compositions have been particularly weak in effect in places poor in air permeability, such as interiors of carpets, sofas, blankets, comforters and bedclothes due to their low volatility even if the effect is achieved in a place on which such an agent is directly spread.

Since the dead bodies and excrements of mites are also allergens, there is a demand for development of an exterminator that not only directly kills mites, but also has a strong 4 repellent effect. Mite eliminators (Japanese Patent Application Laid-Open Nos. 104905/1988 and 87409/1998) containing linalool or carvone of a plant essential oil component that is considered to be comparatively high in safety have been proposed as mite repellents. However, the effects of these agents are also not sufficient.

SUMMARY OF THE INVENTION

It is an object of the present invention to provide a mite repellant and/or miticide composition which can be safely used in residences such as houses, has effects even on the interiors of carpets, sofas and mattresses, exhibits excellent repellent effect and growth-inhibiting effect and also exhibits a mitecidal effect by continuous use.

The present inventors have investigated effects of various plant-derived components on mites and found that jasmonoide, linear sesquiterpene alcohol and linear diterpene alcohol have excellent repellent effect, growth-inhibiting effect and mitecidal effect.

Thus, the present invention provides to a mite repellant and/or miticide composition comprising at least one compound selected from the group consisting of jasmonoide, linear sesquiterpene alcohol and linear diterpene alcohol, and a mite exterminating method making use of this agent.

DETAILED DESCRIPTION OF THE PREFERRED EMBODIMENTS

The mite repellant and/or miticide composition according to the present invention comprises at least one mite repellant and/or miticidely active compound selected from the group consisting of jasmonoide, linear sesquiterpene alcohol and linear diterpene alcohol as an active ingredient.

Non-limiting examples of the jasmonoide include jasmone, dihydrojasmone, lower alkyl esters of jasmonic acid and lower alkyl esters of dihydrojasmonic acid. The term "lower alkyl" as used herein means a linear or branched alkyl group having 1 to 5 carbon atoms, and a methyl group is particularly preferred.

Non-limiting examples of the sesqueterpene alcohol include farnesol and nerolidol.

Non-limiting examples of the linear diterpene alcohol include phytol, isophytol and geranylgeraniol.

Among mite repellant and/or miticidely active compounds jasmone, dihydrojasmone, lower alkyl esters of jasmonic acid, lower alkyl esters of dihydrojasmonic acid, farnesol, nerolidol and phytol are particularly preferred. The mite repellant and/or miticidely active compound is not linalool or carvone.

In the mite repellant and/or miticide composition according to the present invention, at least two of jasmonoide, linear sesquiterpene alcohol and linear diterpene alcohol (hereafter may also be referred to as "active ingredients") may be used.

Examples of the preparation form of the mite repellant and/or miticide composition include preparation forms such as oil, emulsion, hydration, aerosol, transpiration (volatile), fumigant and powder preparations. These active ingredients may be impregnated or directly incorporated into resins, fibrous products, paper, porcelain and the like.

The mite repellant and/or miticidely active compounds may be carried on various liquid or solid carriers when the mite repellant and/or miticide composition according to the present invention is formed into desired preparation forms. No particular limitation is imposed on the liquid carrier so far as it can emulsify or dissolve the mite repellant and/or miticidely active ingredients according to the present invention. However, examples thereof include water, alcohols (methanol, ethanol, isopropanol, etc.), polyhydric alcohols (glycerol, propylene glycol, dipropylene glycol, etc.), ketones (acetone, methyl ethyl ketone, cyclohexanone, etc.), ethers (tetrahydrofuran, dioxane, diethyl ether, etc.), aliphatic hydrocarbons (hexane, kerosene, n-paraffin, isoparaffin, solvent naphtha, etc.) and esters (ethyl acetate, butyl acetate, diethyl acetate, etc.). When the mite repellant and/or miticidely active ingredients are dispersed, emulsified or dissolved in such a liquid carrier, it is preferable to use at least one surfactant selected from polyoxyalkylene alkyl ether sulfates, alkylsulfates, alkylbenzenesulfonates, fatty acid salts, polyoxyalkylene alkyl ethers, alkylglucosides, glycerol fatty acid esters, quaternary ammonium salts, alkylbetaines, amine oxides, etc.

No particular limitation is imposed on the solid carrier so far as it can be impregnated with the mite repellant and/or miticidely active ingredients according to the present invention to hold it. However, examples thereof include those obtained by forming at least one medium selected from inorganic powders (silicic acid, kaolin, bentonite, diatomaceous earth, talc, clay, etc.), organic powders (soybean powder, wheat powder, starch, etc.), inclusion compounds (cyclodextrin, microcapsules, etc.) and solids for impregnation (polypropylene, polyethylene, vinyl chloride, ethylenepolyvinyl alcohol copolymers, polystyrene, polyacrylates, aryl-styrene copolymers, viscose rayon, cellulose and derivatives thereof, pulp, various kinds of paper, nonwoven fabrics, fibers, porcelain, etc.) into powder, granules, sheets or solids.

A fragrance compound may also be suitably contained for the purpose of enhancing a feeling upon use.

The content of the mite repellant and/or miticidely active ingredients in the mite repellant and/or miticide composition according to the present invention may be suitably determined according to the preparation form, application method, application place and the like thereof. In the case of a liquid mite repellant and/or miticide composition in the form of, for example, an oil, emulsion or hydration preparation, the mite repellant and/or miticidely active ingredients are preferably contained in a proportion of 0.001 to 70% by weight, particularly 0.005 to 50% by weight in total.

In the liquid mite repellant and/or miticide composition, a stock liquid containing the mite repellant and/or miticidely active ingredients, a liquid carrier, etc. is preferably formulated into a spray type mite repellant and/or miticide composition of aerosol or pumping type. In the stock liquid, the mite repellant and/or miticidely active ingredients are preferably contained in a proportion of 0.001 to 70% by weight, preferably 0.005 to 50% by weight. As a propellant for the aerosol type mite repellant and/or miticide composition, is preferred LPG, dimethyl ether, nitrogen, carbon dioxide or air. As a pump for the pumping type mite repellant and/or miticide composition, is preferred a pump of trigger type.

In the case of the solid mite repellant and/or miticide composition obtained by carrying the mite repellant and/or miticidely active ingredients on a solid carrier, the mite repellant and/or miticidely active ingredients are preferably contained in a proportion of 0.05 to 100% by weight, particularly 0.01 to 80% by weight.

The mite repellant and/or miticide composition according to the present invention is directly sprayed on mites or sprayed, applied or placed in the form of a liquid or solid on a carpet, sofa, futon or the like to bring it into contact with mites or baits of the mites. Alternatively, the mite repellant and/or miticide composition is sprayed, applied or placed for use on the object such as a carpet; sofa or futon for the purpose of repelling mites.

No particular limitation is imposed on the place or object to be used so far as it is in a house. However, examples thereof include carpets, sofas, futons, pillows, blankets, mattresses, sheets, covers, tatami, cushions, Japanese cushions, stuffed toys, housings such as closets and clog cabinets, and floors.

The mite repellant and/or miticide composition according to the present invention is particularly effective for exterminating mites and ticks inhabiting houses for example, Epidermoptidae such as *Dermatophagoides farinae* Hughes and *Dermatophagoides pteronyssinus* Acaridae such as *Lardoglyphus Konoi, Tyrophagus putresceritiae* and *Aleuroglyphus ovatus*; Glycyphagidae such as *Glycyphagus privatus* Oudemans, *Glycyphagus domesticus* and *Glycyphagus destructor*, Cheyletidae such as *Chelacaropsis moorei* Baker, *Cheyletus maraccensis* Oudemans, *Cheyletus fortis* Oudemands, *Cheyletus eruditus* and *Cheletomrpha lepidopterorum*; Macronyssidae such as *Ornithonyssus bacoti, Ornithonyssus sylviarum*, Dermanyssus such as *Dermanyssus gallinae* and *Dermanyssus hirundinis*; Hapolochthoniidae; Pyemotidae and Sacropidae.

Having generally described this invention, a further understanding can be obtained by reference to certain specific examples which are provided herein for purposes of illustration only and are not intended to be limiting unless otherwise specified.

EXAMPLES

Example 1

The repellent effects of compounds shown in Table 1 were evaluated in accordance with the following method.

1. Mite (or mites) under test: *Dermatophagoides farinae* Hughes.
2. Testing method:

Each test compound was diluted with acetone, black paper 2.5 cm square was impregnated with the diluted test compound in such a manner that the test compound is impregnated in a proportion of 100 $\mu$g or 1,000 $\mu$g per cm$^2$ and the black paper was air-dried under room temperature for 2 hours. Black paper treated with acetone alone was also provided as a control group. Mites grown at high density were transferred together with a medium to a glass batt (15×20 cm), and a sheet of gauze cut out in the same size was placed thereon. This medium was placed in a plastic closed container controlled at relative humidity of at least 85% with saturated brine and incubated at 25° C. Three sheets of the black paper treated with the test compound were arranged side by side at intervals of at least 5 mm on the gauze to count the number of the mites climbed up the front and back surfaces of the black paper after 15 minutes. This process was repeated 3 times to find an average value, and it was compared with the control group to calculate out a repelling rate in accordance with the following equation.

Repelling rate=$\{(A-B)/A\}\times 100(\%)$ wherein A is the number of mites climbed up in the control group, and B is the number of mites climbed up in the treated group.

|  | Test compound | Concentration of compound ($\mu$g/cm$^2$) | |
|---|---|---|---|
|  |  | 1,000 | 100 |
| Invention | cis-Jasmone | 85 | 72 |
|  | Methyl jasmonate | 97 | 93 |
|  | Dihydrojasmone | 83 | 80 |
|  | Methyl dihydrojasmonate | 94 | 90 |
|  | Farnesol | 96 | 94 |
|  | Nerolidol | 79 | 80 |
|  | Phytol | 72 | 52 |
| Comparative | Carvone | 29 | 10 |
|  | Linalool | 57 | 47 |

Example 2

The miticidal effects of compounds shown in Table 2 were evaluated in accordance with the following method.

1. Mite or Mites under test: *Dermatophagoides farinae* Hughes.
2. Testing method:

Each test compound was diluted with acetone, filter paper 5×10 cm in size was impregnated with the diluted test compound in such a manner that the test compound is impregnated in a proportion of 1,000 $\mu$g per cm$^2$, and the filter paper was air-dried at room temperature for 2 hours. Filter paper treated with acetone alone was also provided as a control group. Each filter paper was folded in two, and 20 to 40 mites were freed therein to close the open portion with aclip in such a manner that the mites cannot escape. After the filter paper was incubated for 24 hours or 48 hours in an environment of 25° C. and relative humidity of at least 80%, the numbers of the living or dead mites are calculated through a stereoscopic microscope. This process was repeated 3 times to find an average lethality, and it was compared with the untreated group to calculate out a compensated lethality in accordance with the following equation.

Compensated lethality=$\{(Y-X)/(100-X)\} \times 100$ (%)

wherein X is an average lethality in the control group, and Y is an average lethality in the treated group.

TABLE 2

| | | Compensated lethality (%) | |
|---|---|---|---|
| | | Incubation time | |
| | Test compound | 24 hr | 48 hr |
| Invention | Methyl dihydrojasmonate | 100 | 100 |
| | Farnesol | 63 | 77 |

Example 3

The inhibitory effect of methyl dihydrojasmonate on the growth of mites was evaluated in accordance with the following method.
1. Mite (or Mites) under test: *Dermatophagoides farinae* Hughes.
2. Testing method:

After a predetermined amount of methyl dihydrojasmonate diluted with ethanol was added to mite-free sterilized medium (10 g; MF powder feed; Oriental Yeast Co., Ltd.), and both were mixed, the mixture was air-dried at room temperature for at least 3 hours to provide a treated group. A medium mixed with ethanol was provided as a control group. Mites sufficiently grown with the same medium as described above were fully mixed with the medium, and this mixture (1 g) was mixed into the test medium containing methyl dihydrojasmonate and control medium, respectively. After fully stirred, the mites were raised at 25° C. for 22 days. A sample (0.1 g) was taken out of each medium to count the number of active mites through a microscope, thereby calculating out a mite growth-inhibiting rate. Incidentally, the test was repeated 3 times to conduct the evaluation in terms of the average value thereof.

Mite growth-inhibiting rate=$\{(T-S)/T\} \times 100$ (%)

wherein T is the number of viable mites in the control group, and S in the number of viable mites in the treated group.

TABLE 3

| | Mite growth-inhibiting rate (%) | |
|---|---|---|
| Concentration of methyl dihydrojasmonate in medium (% by weight) | Growth-inhibiting rate on the 8th day (%) | Growth-inhibiting rate on the 22nd day (%) |
| 0.045 | 75 | 54 |
| 0.12 | 86 | 61 |
| 0.23 | 93 | 69 |
| 0.34 | 92 | 80 |

Example 4

The following formulation was charged in a can to prepare an aerosol preparation of a mite repellant and/or miticide composition.

| | |
|---|---|
| Methyl dihydrojasmonate | 0.5 (% by weight) |
| Ethanol | 49.5 |
| LPG | 50 |

Example 5

A spray preparation of trigger type was prepared in accordance with the following formulation.

| | |
|---|---|
| Farnesol | 1 (% by weight) |
| Laurylglucoside | 1 |
| Ethanol | 20 |
| Water | 78 |

Example 6

The same liquid as in Example 5 was prepared to provide a stock liquid for impregnation into paper. This stock liquid (100 parts by weight) was impregnated into a nonwoven fabric (100 parts by weight), and the impregnated fabric was installed on a mop to produce a mop type cleaner for floor.

Example 7

A mite repellant and/or miticide composition in the form of powder was prepared in the following formulation.

| | |
|---|---|
| Cis-Jasmone | 5 (% by weight) |
| Nerolidol | 5 |
| Silicic anhydride | 5 |
| Talc | 85 |

Example 8

A stock liquid for impregnation was prepared in accordance with the following formulation. This stock liquid (100 parts by weight) was impregnated into a clay plate (1000 parts by weight) to prepare a mite repellant and/or miticide composition of plate-carried type.

| <Stock liquid for impregnation> | |
|---|---|
| Phytol | 50 (% by weight) |
| Isoparaffin solvent | 50 |

INDUSTRIAL APPLICABILITY

The mite repellant and/or miticide compositions according to the present invention have excellent repellent effect, growth-inhibiting effect and mite repellant and/or miticide effect on mites inhabiting houses.

Obviously, numerous modifications and variations of the present invention are possible in light of the above teachings. It is therefore to be understood that within the scope of the appended claims, the invention may be practiced otherwise than as specifically described herein.

This application is based on Japanese patent application 2001-094696 and 2001-373554 filed in the Japanese Patent Office on Mar. 29, 2001 and Dec. 7, 2001 the entire contents of which are hereby incorporated by reference.

What is claimed as new and desired to be secured by Letters Patent of the United States is:

1. A mite repellant composition consisting essentially of:
   i) at least one mite repellant compound selected from the group consisting of jasmonoides, linear sesquiterpene alcohols and linear diterpene alcohols;
   ii) a carrier, wherein said carrier is a polyhydric alcohol selected from the group consisting of glycerol, propylene glycol, dipropylene glycol and a mixture thereof; and iii) a surfactant selected from the group consisting of polyoxyalkylene alkyl ether sulfates, alkylsulfates, alkylbenzenesulfonates, fatty acid salts, polyoxyalkylene alkyl ethers, alkylglucosides, glycerol fatty acid esters, quaternary ammonium salts, alkylbetaines, amine oxides and a mixture thereof.

2. The mite repellant composition according to claim 1, wherein said mite repellant compound is selected from the group consisting of jasmone, dihydrojasmone, a lower alkyl ester of jasmonic acid or a lower alkyl ester of dihydrojasmonic acid, farnesol, nerolidol, phytol and a mixture thereof.

3. The mite repellant composition according to claim 1, wherein said at least one mite repellant compound is present in an amount effective to repel mites inhabiting houses.

4. The mite repellant composition of claim 1, wherein said mite repellant compound is present in an amount of from 0.001 to 70% by weight.

5. The mite repellant composition of claim 1, wherein said composition is a preparation in a form selected from the group consisting of oil, emulsion, hydration, transpiration (volatile), fumigant and powder preparations.

6. A mite repellant composition consisting essentially of:
   i) at least one mite repellant compound selected from the group consisting of jasmonoides, linear sesquiterpene alcohols and linear diterpene alcohols;
   ii) a carrier, wherein said carrier is a solid carrier selected from the group consisting of silicic acid, kaolin, bentonite, diatomaceous earth, talc, clay, soybean powder, wheat powder, starch, cyclodextrin, microcapsules, polypropylene, polyethylene, vinyl chloride, ethylenepolyvinyl alcohol copolymers, polystyrene, polyacrylates, aryl-styrene copolymers, viscose rayon, cellulosics, pulp, papers, nonwoven fabrics, fibers, porcelain and a mixture thereof; and
   iii) a surlactant selected from the group consisting of polyoxyalkylene alkyl ether sulfates, alkylsulfates, alkylbenzenesulfonates, fatty acid salts, polyoxyalkylene alkyl ethers, alkylglucosides, glycerol fatty acid esters, quaternary ammonium salts, alkylbetaines, amine oxides and a mixture thereof.

7. A mite repellant composition consisting essentially of:
   i) at least one mite repellant compound selected from the group consisting of jasmonoides, linear sesquiterpene alcohols and linear diterpene alcohols;
   ii) a carrier; and
   iii) a surfactant selected from the group consisting of polyoxyalkylene alkyl ether sulfates, alkylsulfates, alkylbenzenesulfonates, fatty acid salts, polyoxyalkylene alkyl ethers, alkylglucosides, glycerol fatty acid esters, quaternary ammonium salts, alkylbetaines, amine oxides and a mixture thereof;
   wherein said carrier is a solid carrier and said mite repellant compound is present in an amount of from 0.05 to 100% by weight.

8. A method of exterminating mites, tick or both comprising: applying a mite repellant composition consisting essentially of i) at least one mite repellant compound selected from the group consisting of jasmonoides, linear sesquiterpene alcohols and linear diterpene alcohols; ii) a carrier and iii) a surfactant selected from the group consisting of polyoxyalkylene alkyl ether sulfates, alkylsulfates, alkylbenzenesulfonates, fatty acid salts, polyoxyalkylene alkyl ethers, alkylglucosides, glycerol fatty acid esters, quaternary ammonium salts, alkylbetaines, amine oxides and a mixture thereof, to a place or object in need thereof.

9. The method of claim 8, wherein said place or object in need thereof is located within a residence.

10. The method of claim 8, wherein said mite repellant composition is a preparation in a form selected from the group consisting of oil, emulsion, hydration, transpiration (volatile), fumigant and powder preparations.

11. A method of exterminating mites, tick or both comprising: applying a miticide composition consisting essentially of at least one miticidely active compound selected from the group consisting of jasmonoides, and linear diterpene alcohols, to a place or object in need thereof.

12. The method of claim 11, wherein said place or object in need thereof is located within a residence.

13. A mite repellant composition consisting essentially of:
   i) at least one mite repellant compound selected from the group consisting of jasmonoides, and linear diterpene alcohols;
   ii) a carrier, wherein said carrier is a liquid carrier; and
   iii) a surfactant selected from the group consisting of polyoxyalkylene alkyl ether sulfates, alkylsulfates, alkylbenzenesulfonates, fatty acid salts, polyoxyalkylene alkyl ethers, alkylglucosides, glycerol fatty acid esters, quaternary ammonium salts, alkylbetaines, amine oxides and a mixture thereof.

14. The mite repellant composition according to claim 13, wherein said mite repellant compound is selected from the group consisting of jasmone, dihydrojasmone, a lower alkyl ester of jasmonic acid or a lower alkyl ester of dihydrojasmonic acid, phytol and a mixture thereof.

15. The mite repellant composition according to claim 13, wherein said at least one mite repellant compound is present in an amount sufficient to repel mites inhabiting houses.

16. The mite repellant composition of claim 13, wherein said carrier is a liquid carrier selected from the group consisting of water, alcohols, polyhydric alcohols, ketones, ethers, aliphatic hydrocarbons and esters.

17. The mite repellant composition of claim 16, wherein said carrier is an alcohol selected from the group consisting of methanol, ethanol, isopropanol and a mixture thereof.

18. The mite repellant composition of claim 16, wherein said carrier is a polyhydric alcohol selected from the group consisting of glycerol, propylene glycol, dipropylene glycol and a mixture thereof.

19. The mite repellant composition of claim 13, wherein said mite repellant compound is present in an amount of from 0.001 to 70% by weight.

20. The mite repellant composition of claim 13, wherein said composition is a preparation in a form selected from the group consisting of oil, emulsion, hydration, transpiration (volatile), fumigant and powder preparations.

21. A mite repellant composition consting essentially of:
   i) at least one mite repellant compound selected from the group consisting of jasmonoides, and linear diterpene alcohols; and
   ii) a carrier, wherein said carrier is a solid carrier selected from the group consisting of silicic acid, kaolin, bentonite, diatomaceous earth, talc, clay, soybean powder, wheat powder, starch, cyclodextrin, microcapsules, polypropylene, polyethylene, vinyl chloride, ethylenepolyvinyl alcohol copolymers, polystyrene, polyacrylates, aryl-styrene copolymers, viscose rayon, cellulosics, pulp, papers, nonwoven fabrics, fibers, porcelain and a mixture thereof.

22. The mite repellant composition of claim 21, wherein said mite repellant compound is present in an amount of from 0.05 to 100% by weight.

23. A method of exterminating mites, tick or both comprising: applying a mite repellant composition consisting essentiallt of at least one mite repellant compound selected from the group consisting of jasmonoides, and linear diterpene alcohols, to a place or object in need thereof.

24. The method of claim 23, wherein said place or object in need thereof is located within a residence.

25. The method of claim 23, wherein said mite repellant composition is a preparation in a form selected from the group consisting of oil, emulsion, hydration, transpiration (volatile), fumigant and powder preparations.

* * * * *